United States Patent [19]

Macklem

[11] 4,409,182
[45] Oct. 11, 1983

[54] COLORIMETER TEST KIT APPARATUS

[76] Inventor: F. Sutherland Macklem, 468 Main St., New Canaan, Conn. 06840

[21] Appl. No.: 162,044

[22] Filed: Jun. 23, 1980

[51] Int. Cl.³ .................... G01N 21/78; G01N 21/80
[52] U.S. Cl. .................................. 422/61; 206/45.34;
206/230; 206/459; 206/499; 356/421; 356/422;
422/58; 436/110; 436/125; 436/163
[58] Field of Search .............. 23/230 R; 422/102, 68,
422/61, 55, 58; 206/45.34, 446, 499, 459, 230;
356/42, 421, 422, 423, 424

[56] References Cited

U.S. PATENT DOCUMENTS

| | | | |
|---|---|---|---|
| 2,009,943 | 7/1935 | Munsell et al. | 356/421 |
| 2,027,816 | 1/1936 | Drucker | 356/423 X |
| 3,121,613 | 2/1964 | Bittner | 23/230 R |
| 3,226,196 | 12/1965 | La Vietes | 23/917 X |
| 3,446,596 | 5/1969 | Salivar et al. | 23/230 R |
| 3,579,306 | 5/1971 | Crane | 23/230 B |
| 3,747,830 | 7/1973 | Goldman | 206/45.34 X |
| 3,813,222 | 5/1974 | La Vietes | 23/917 X |
| 3,910,764 | 10/1975 | Tower | 422/61 |
| 3,937,613 | 2/1976 | Rosicky | 23/230 R X |
| 4,073,623 | 2/1978 | Bodart | 422/55 |
| 4,125,376 | 11/1978 | Razulis | 23/230 R |
| 4,195,059 | 3/1980 | Whitcher et al. | 422/61 |

FOREIGN PATENT DOCUMENTS 1556082 11/1979 United Kingdom ............... 422/102

*Primary Examiner*—Arnold Turk

[57] ABSTRACT

A method and apparatus for the colorimetric testing of non-opaque fluids that comprises compact test kit apparatus made from readily available plastic components, and sets of such test kits made even more compact by a combination of chemistries for certain tests that simplifies and improves the accuracy of those tests while reducing the number of test kits required in a set. The colorimeter component of each test kit provides non-opaque colored plastic windows made from readily available commercial materials that are accurately color controlled. The colorimeter also makes automatic correction of the color windows to compensate for any initial coloration in the fluid being tested. The colorimeter also serves as the container for one complete kit and allows a set of kits to hang from closely spaced hooks to conserve space and make them exceptionally convenient to use. The use of readily available commercial components and materials avoids the expense of special tooling but more particularly eliminates the high costs usually associated with the very accurate color control needed by good colorimeters. The kit also has reagent containers that can be closed at negative pressure and hermetically sealed until the user converts them into dropper vials. Structurally the kit comprises tubular reagent container vials that nest with tubular sampler vials that nest with the tubular colorimeter with its non-opaque color patch windows.

8 Claims, 4 Drawing Figures

COLORIMETER TEST KIT APPARATUS

BACKGROUND

Colorimetric testing of all kinds of fluids from water to blood has long been a standard method of chemical testing. Inexpensive colorimetric test kits have been made for testing swimming pool water and for the smaller but more demanding aquarium hobby. In the aquarium hobby colorimetry is used to test water not only for chlorine and pH (i.e. acidity) but also for ammonia, phosphate, carbonates, copper, and other properties, impurities, and pollutants. But aquarium test kits have mostly comprised nothing more than a box containing one or two small dropper bottles of reagents, one or two sampler vials, and color patches printed on an opaque instruction card. With the growth of the even smaller but more demanding saltwater aquarium hobby it became obvious that attempting to match the color of light transmitted through colored water to the color of light reflected from opaque color patches printed on paper was crudely inadequate. A notable attempt to provide a more adequate colorimeter and set of test kits was made in Germany and sold here under the name Tetra Test. It proved to be much too expensive for wide acceptance in the aquarium hobby and it was too elaborate for the swimming pool industry.

In the German "Tetra Test" set of test kits the colorimeter comprised a plastic holder into which two specially designed rectangular sampler vials could be inserted and a color wheel mounted. Each color wheel comprised a plastic disc with a ring of non-opaque colored plastic chips to present a selectable color window. The plastic holder held one sampler vial behind the color wheel with the other sampler vial adjacent to it. The water in the sampler vial behind the color wheel was left untreated and it served to correct the window color to compensate for any initial coloration in the water being tested. Reagents were added to the water sample in the adjacent vial and the color that developed was compared to the color windows which were brought into position in front of the untreated vial by turning the color wheel. While this made an excellent colorimeter in principle, it was too expensive partly because the small market to which it was addressed could not justify the capital investment for the required tooling. It also was and is practically impossible to accurately control the color of plastic chips except at prohibitive cost. Accordingly it is an object of my invention to drastically reduce these sources of cost by using readily available commercial components and materials in a colorimeter test kit apparatus that is equal or superior to the "Tetra Test" system in principle and in performance. Other objects and advantages of my colorimeter test kit apparatus and method are described in the summary or will be obvious to those skilled in the art.

Colorimetric test kits have also been adapted to the aquarium hobby with a standard form of colorimeter found in professional laboratories. The colorimeter consists of so-called Nessler Tubes mounted in a plastic holder into which a sampler vial can be inserted for color comparison. Nessler Tubes are glass tubes filled with colored water. A Nessler Tube colorimeter is therefore bulky, expensive, and subject to breakage. For the aquarium hobby such colorimeters are commonly limited to no more than two or three Nessler Tubes in an effort to minimize costs. Even then they are still too expensive, and too bulky, to have found wide acceptance in the aquarium hobby. Since the aquarist is faced with the need to test for many different things he requires many test kits, and a set of bulky test kits is obviously unattractive and inconvenient. Nessler Tube test kits and the "Tetra Test" system overcome the inadequacy of the opaque color patches in cheap kits by providing a better colorimeter but they do not solve other problems. They still consist of one or two dropper bottles of reagents, with sampler vials, and they are bulkier than ever because of the addition a colorimeter apparatus in place of the cheap color patch card. They also retain the problem that dropper bottles are unsuited to holding some of the more volatile reagents which easily evaporate. It is an object of my invention to provide a test kit made of commercially available parts that cooperate to eliminate many problems including the bulkiness and the use of unsealable dropper bottles, while at the same time providing a true colorimeter with color windows and automatic color compensation.

SUMMARY

With respect to present colorimetric test kits some of the aims of my invention are to produce a test kit that, (1) is less expensive to make in small or large quantities, (2) is much less bulky, (3) has a more accurate colorimeter, (4) allows compensation of the colorimeter for initial coloration in the fluid being tested, (5) requires fewer kits for a given set of tests, (6) has sealable vials for volatile reagents and (7) is more convenient to use as a single kit or in a set of kits. I call my invention a color tube test kit for reasons that will become obvious and a trademark registration of the name COLORTUBE has been applied for. Meanwhile it is a convenient name to use here in describing my invention and I will henceforth refer to it using the name color tube.

The principal mechanical components of my color tube test kit are tubular plastic containers commercially available from many sources such as Flex Products Co. of Carlstadt N.J., or Petro Plastics of Garwood N.J. They are transparent plastic tubes closed at one end to form a container which can be supplied leak-proof on special order. Plastic caps or plugs are supplied for closing the open end. I use one such transparent tubular container as the main or outer container for my color tube test kit, and it carries on it a set of non-opaque color windows. The color windows are cut from commercially available sheets of non-opaque color-printed plastic film which has a pressure sensitive adhesive on one side that hold the color windows on the color tube. Since these plastic film sheets are made for the graphic arts industry they are very accurately color controlled, but since they are manufactured in large quantity they are relatively inexpensive even in retail stores. They are available from almost any art store or graphic arts supply house and they come in a wide range of colors and shades. Thus it is usually possible to select color sheets that perfectly or almost perfectly match the colors developed in various colorimetric tests. To obtain a perfect match it is possible to modify the test reagents by the addition of a small amount of suitable dye color.

The color tube with its color windows in place serves the combined function of main container for the whole color tube test kit and as the very accurate colorimeter component of the kit. The need, in some cases, to modify a reagent by adding a small amount of dye to it in order to achieve high accuracy with a available color window material leads to a further improvement since"

the added dye can itself be a reagent that is sensitive to some other chemical property. Thus making a colorimetric test match a set of commercially available color windows ends up with combining tests for two different things in one test kit. This is more fully explained with an example in the detailed description. Suffice it to say here that by using the available accurately controlled color sheets to make the color windows, and adjusting the reagents to match the available colors, a combination of tests results which reduces the number of kits needed for a given set of tests. It can also make a qualitative change in the color response that tends to minimize an important source of error, as will also be explained more fully in the detailed description.

Thus the color tube combines the function of container for the whole test kit with the colorimeter function and, by having it made leakproof, it also serves as the color compensation vial since it can be filled with the fluid under test. As a kit container it has the particular advantage that it can be supplied with a hang-up plug for closing the open end. This makes the color tube kit not only much less bulky than any other kits, but it allows a set of color tube kits to hang alongside one another making them exceptionally convenient to use as a set for performing a set of tests. The greatly reduced bulk also has the very important advantage that it permits dealers and distributors to store the kits in refrigerators which, in many cases, is necessary to preserve the useful life of the reagents almost indefinitely.

The leakproof color tube which serves as kit container and colorimeter eliminates the need for an auxiliary sampler vial to hold untreated fluid behind the color windows to compensate for initial coloration in the fluid being tested. It is only necessary to fill the color tube with the untreated fluid and that automatically places the fluid behind the color windows to compensate for initial fluid coloration. In addition there are blank transparent spaces between the color windows so that the color of the test sample, in some tests, can be compared directly with the clear untreated fluid being tested. This is very important in those tests where very pale color traces have to be detected as, for example, when testing for low levels of ammonia. A test sample with a low level of ammonia will develop a very pale trace of yellow color which, by itself, will seem to be colorless. When it is compared against the clear fluid in the transparent colortube, however, the trace color is easily detected.

The transparent plastic tubular containers used in my color tube test kits are available in sequential sizes. The largest sized outer tube that serves as the container for the whole kit is the color tube colorimeter. For sampler vials I used the next smaller size transparent tubular container. The sampler vial is a short tube open at one end and has a line on it showing the level to which it must be filled for the test. When not in use the sampler vial fits inside the color tube. Reagents are contained in vials of the next smaller size. Thus when not in use the sampler vial or vials sit in the color tube and reagent vials sit in the sampler vials. It is this nesting construction, together with the multiple function of the color tube, that makes the kits so dramatically compact that dealers and distributors can afford to keep them in precious refrigerator space.

The color tube and the sampler vial or vials must, of course, be transparent. That is not so for the reagent vials. On the contrary many of the reagents are deteriorated by light. Also the transparent tubular containers are made of a plastic (cellulose acetate) that is not resistant to some of the chemical reagents. The reagent vials are then best made of a highly resistant plastic such as polyethylene or polypropylene. Tubular containers in this material are not generally commercially available, but the raw tubing is or it can be inexpensively extruded using standard dies. The plugs supplied with regularly available transparent containers are made of polyethylene and are therefore suitable for use with polyethylene or polypropylene tubing to form containers.

The regular polyethylene closure plugs are of course solid, whereas the reagents have to be made available in drops. Ordinary test kits therefore put the reagents in dropper bottles, but that causes problems with reagents that deteriorate due to oxidation or that evaporate easily. In my color tube test kits I use the solid closures for the reagent vials but include with each kit common map tacks, appropriately colored for identification. The user converts the reagent vials into dropper vials by pushing a map tack through the soft polyethylene closure plug. With the hole left by the map tack when it is removed, the vial can be used to deliver drops of reagent to the fluid sample. The solid closure plug allows the reagent vials to be closed, initially, at negative pressure to prevent leakage, and for highly volatile reagents it allows the vials to be heat sealed in a heat sealing jig that melts the plastic to form a hermetic closure.

BRIEF DESCRIPTION OF THE DRAWINGS

FIG. 4 is a front axial sectional view of a reagent vial.

DETAILED DESCRIPTION OF THE INVENTION

Figure 1:
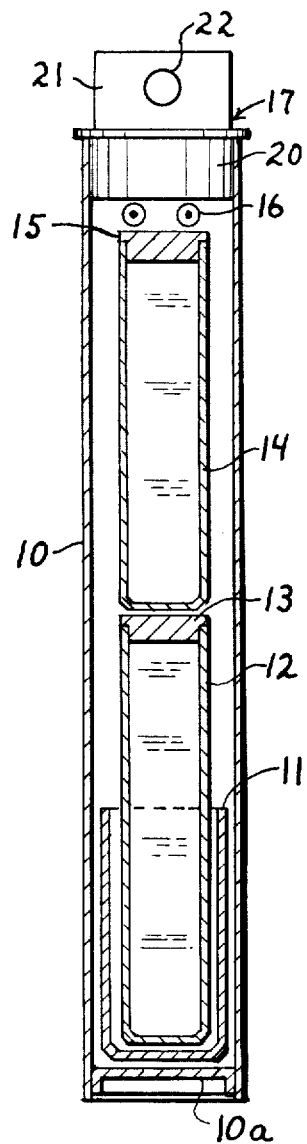
FIG. 1 is a front axial sectional view of the assembled condition of the various elements of my colorimeter test kit.

Referring to FIG. 1 there is shown the transparent tubular container 10 which is the color tube closed at its lower end by a suitable sealed-in closure plug 10a. Disposed in the lower portion of the tubular container or color tube 10 is a sampler vial 11 closed at one end and open at the other end. Disposed in nesting relation with the sampler vial 11 is a reagent vial 12 which is closed at one end and has a tightly fitting closure plug 13 at the other end. The plug 13 is made of any suitable puncturable material such as polyethylene plastic. The reagent vial 12 is made of any suitable semi-rigid material such as polyethylene or polypropylene. A second reagent vial 14 similar to vial 12 is also disposed within the color tube 10, the vials 12 and 14 containing the necessary reagents for making a colorimetric test. If necessary one or both of the vial closure plugs 13 and 15 may be heat sealed in place. The color tube also contains two tack members 16 for puncturing the closure plugs 13 and 15. The upper end of the color tube is closed by a tight fitting plug 17 that is formed so that it is adapted to be removably wedged into the open end of the color tube 10 and is formed with an upper planar tab 21 having a hole 22 formed therein which facilitates hanging the kit for user or store display purposes.

Figure 2:
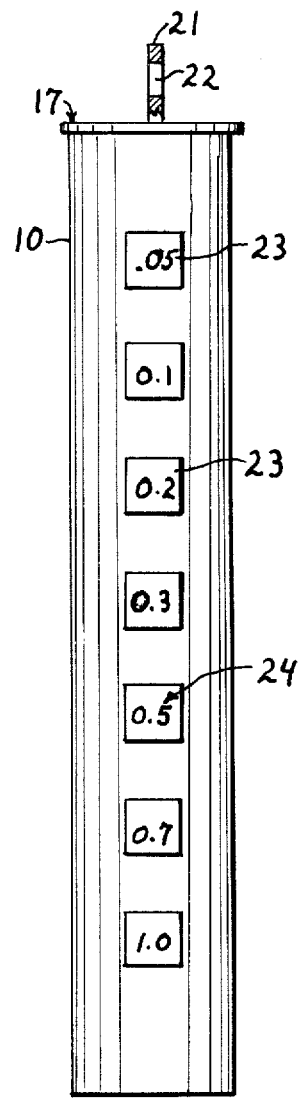
FIG. 2 is a side elevational view of the color tube and illustrates an array of color windows on the outer surface of the color tube which is the kit container.
Figure 3:
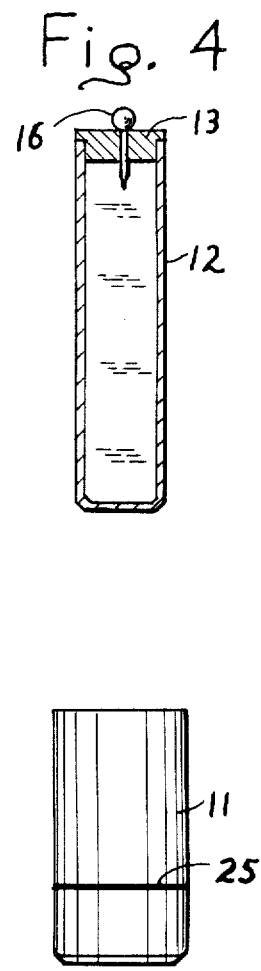
FIG. 3 is a front elevational view of a sampler vial.

The color tube 10 is provided with an array of color windows on its outer surface shown in FIG. 2. The color windows are printed colors on the plastic film patches 23 which are secured to the outer surface of the tube 10 by any suitable means such as pressure sensitive adhesive. The color patches 23 are non-opaque colored plastic film of predetermined colors and have numbers 24 to indicate corresponding respective quantitative results of a particular colorimetric test that develops a matching color in a fluid in the sampler vial 11. The sampler vial 11 is provided with a sample level line 25 as shown in FIG. 3. The tack member 16 may be used to puncture the plugs 13 and 15 as illustrated in FIG. 4, so as to afford a hole through which reagent fluid may be dispensed drop by drop by squeezing the reagent vial 12 so as to add reagent to the sample in the sampler vial 11. For the two reagent vials 12 and 14 two tack members are provided to also serve as hole plugs, as indicated in FIG. 4, when the kit is not in use. The numbers 24 associated with the color windows are printed directly on the outer surface of the color tube since the color patches 23 are non-opaque and do not conceal the associated numbers. The colors printed on the color patches could also be printed directly on the outer surface of the color tube, if quantities required warranted that, since these colors are available in standardized and carefully controlled printing inks, which reduce but does not entirely eliminate the problem of color control because density must still be carefully controlled.

It was found that the reagent vials closed with tight fitting polyethylene plugs were subject to leakage in transit. This problem is overcome with heat sealing, of course, but heat sealing is a quite complex, relatively slow, and expensive procedure requiring special equipment. The leakage can also be eliminated by filling the vials in a simple compression jig that keeps them compressed until they are closed. The compression is released when the vials are removed from the filling jig which leaves them with a negative internal pressure. Unless the reagent is highly volatile, therefore, I prefer to eliminate the leakage problem by closing the vials at negative pressure. Sealant cements were also tried but these tended to discolor the reagents in time and the effort to find a suitable sealant was finally abandoned in favor of negative pressure or heat sealing. If the reagent vials are closed with negative pressure or heat sealing they can be formed of tubing and closed with tight fitting plugs at both ends instead of being molded with one end closed as shown in the drawing. The tubing is less expensive than molded vials.

In those cases where standardized colors for the color windows do not perfectly match the color developed by a particular colorimetric test, the reagents can be modified by the addition of a small amount of a suitable dye, and when this can be done it is possible in some cases to combine more than one test in one colorimetric test kit. How this is accomplished is best explained by describing a particular case, and a typical case in which color adjustment is necessary and in which two tests can be combined in one kit is the so-called DPD test for chlorine which I shall now describe. To test for chlorine in water the user fills the sampler vial to the line with a sample of the water to be tested. To this he adds two drops of a first reagent (weak solution of potassium iodide) and follows with two drops of the DPD reagent. The color that develops is a bluish purple, or magenta, the depth of intensity of which depends on the amount of chlorine present in the sample. The basic blue magenta color, however, is not well matched by the available standard colors. Here it may be noted that as in many colorimetric tests the change in color is only a change in intensity or density of a constant hue. Such tests are subject to quantity errors, that is, if the water sample is slightly too large it dilutes the color and gives a false result, or if the amount of reagent varies due to variation in drop size this also dilutes or intensifies the color to give a false result. Quantity errors of this kind are minimized if the test produces a change in hue rather than just a change in color density. The change in hue can be observed more or less independently of small differences in the density.

The chlorine test can be modified by adding a yellow dye to the first reagent (the weak potassium iodide solution). This results in a test which for zero chlorine is yellow and as chlorine content is increased it changes from yellow through orange and red to magenta and purple. The choice of yellow dye is arbitrary since colorimetric tests are highly specific, that is, they are not affected by the presence of chemicals other than the one being tested for which, in this case is chlorine. Thus practically any yellow dye that does not contain chlorine is suitable. The dye can therefore be a dye indicator such as, for example, phenol red, which is yellow in an acid fluid and changes through orange to red as the pH of the fluid (the acidity) changes. Such dyes are called indicator dyes because they are used to indicate pH. The DPD solution, which is the second reagent, is highly acidic, therefore when the DPD is added to the sample the sample will be acid and the dye indicator (phenol red) will add yellow to the result. But in the first solution the phenol red is a pH indicator. Thus when the first solution is added it indicates the pH of the water sample and when the second solution is added it indicates the chlorine content of the water. The pH test and the chlorine test are thereby combined in one test so that one less test kit is required for a given set of tests. Most swimming pools are checked only for pH and chlorine therefore this procedure gives a single colorimetric test kit that will make both measurements that swimming pools require. It also results in a set of colors that can be perfectly matched with available standardized colors for the color windows. The method of adjusting the reagent color to match the available standard colors of my colorimetric test kit is widely applicable because of the specificity of colorimetric tests. For the same reason it is possible to make the necessary adjustment and at the same time combine more than one test in one test kit as in the particular case described.

Another case in which the addition of the phenol red dye indicator can be used to combine two tests is in testing for nitrite. The standard test for nitrite uses two reagents, sulfanilic acid and dihydrochloride. The phenol red is added to the dihydrochloride. The dye modified dihydrochloride is added to the sample first. The phenol red develops color in response to the pH of the sample. Then the sulfanilic acid is added to the sample to check for nitrite.

It will be seen that I have described a colorimetric test kit apparatus and method that can be manufactured using readily available commercial components and materials, and the apparatus and method that I have described achieves a dramatic reduction in cost and bulk, as a single kit or as a reduced set of kits. A typical kit such as is illustrated schematically in the Figure drawings uses a color tube that measures 7 inches by ⅜th of an inch with either a round or a square cross section. The vials in such a kit hold about ¼ ounce of reagent each, if there are two of them. The color tube, typically, has seven or eight color windows in addition to clear transparent spaces which allow it to still serve as a blank comparison vial for those tests in which a very slight color trace must be detected, as for example when testing for ammonia.

I claim:

1. A colorimetric test kit apparatus comprising a color tube which includes a transparent plastic tubular container having one end closed and leak proof, said tube being provided with an array of non-opaque color windows on its surface, the color of the color windows being selected to at least approximately match the colorimetric response of a measured sample of fluid under test, which color tube can be filled with the fluid under test so as to correct the color of the color windows for any initial coloration of the fluid under test; at least one transparent plastic tubular sample container marked with a sample level line to be used as a sampler vial to provide an accurately measured sample of the fluid under test; at least one hermetically sealed tubular reagent vial containing a chemical reagent; puncturing means for opening said vial to provide a hole of predetermined size to convert it to a dropper to dispense said chemical reagent drop by drop into the measured sample in the sampler vial to develop a colored sample which can be held adjacent to one color window at a time to find the best color match; said tubular reagent vial being disposed in said sampler vial and said sampler vial being disposed in said color tube in a nesting arrangement so that said color tube becomes a holder for the complete test kit when not in use; and removable cap or plug means for closing said color tube, said cap or plug being of a form and size such that the complete test kit can be positioned by hanging closely alongside similar kits to present a conveniently accessible array of colorimetric test kits such as may be required in analyzing a given fluid.

2. Apparatus as defined by claim 1 additionally comprising a second reagent vial containing a second chemical reagent for colorimetric tests requiring two reagents; said second reagent vial also being disposed in said color tube when not in use.

3. Apparatus as defined by claim 1 wherein said puncturing means comprises at least one tack-like member means.

4. Apparatus as defined by claim 1 wherein said color windows are printed with colored printing inks selected from standardized colors.

5. Apparatus as defined by claim 1 wherein said color windows are cut from color printed plastic film sheets and are secured to the outer surface of said color tube by transparent adhesive means.

6. Apparatus as defined by claim 1 wherein said at least one reagent vial is made of polyethylene or polypropylene plastic material.

7. Apparatus as defined by claim 1 wherein said at least one reagent vial includes as a chemical reagent a dye modified to make the test results match available selected colored printing inks or colored plastic film sheets used to form color windows, said dye modification having itself a colorimetric response so as to effect an additional colorimetric test on a single fluid sample.

8. Apparatus as defined by claim 7 wherein the dye modifier is additionally chosen so as to effect a hue change in a colorimetric test that would otherwise develop only a change in color density.

* * * * *